United States Patent [19]

Loozen

[11] Patent Number: 5,019,585

[45] Date of Patent: May 28, 1991

[54] TRICYCLIC AROMATASE INHIBITORS

[75] Inventor: Hubert J. J. Loozen, Uden, Netherlands

[73] Assignee: Akzo N.V., Arnhem, Netherlands

[21] Appl. No.: 405,917

[22] Filed: Sep. 12, 1989

[30] Foreign Application Priority Data

Sep. 12, 1988 [NL] Netherlands .................. 8802227

[51] Int. Cl.$^5$ ........................................... C07C 69/76
[52] U.S. Cl. .................................. 514/396; 514/399; 548/335; 548/341
[58] Field of Search ............... 548/335, 341, 346; 514/396, 399

[56] References Cited

U.S. PATENT DOCUMENTS 4,564,698  1/1986  Wieringa et al. .............. 514/231.1

FOREIGN PATENT DOCUMENTS 41293  12/1981  European Pat. Off. .

OTHER PUBLICATIONS

CA (Chemical Abstracts Service) 96:122465h of EU 41293.

Primary Examiner—Frederick E. Waddell
Assistant Examiner—Catherine S. Kilby Scalzo
Attorney, Agent, or Firm—William M. Blackstone

[57] ABSTRACT

The invention relates to tricyclic aromatase inhibitors, their preparation and their use in a pharmaceutical preparation.

The compounds according to the invention possess the general formula I

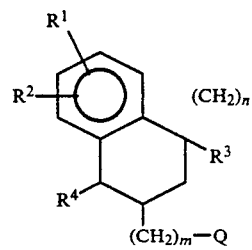

wherein $R^1$ and $R^2$ independently of one another denote H, halogen, alkyl, alkoxy, alkylthio, OH, CN, $CF_3$, $NO_2$, an amino group which is unsubstituted or substituted by alkyl, an NHacyl group, carbonamide or a free or esterified carboxylate group;

$R^3$ is H, alkyl, alkoxyalkyl or arylalkyl;

$R^4$ is H, OH, alkoxy or arylalkoxy;

m is 1 or 2;

n is 2, 3 or 4;

the broken line represents an optional bond;

Q denotes

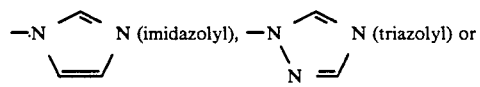

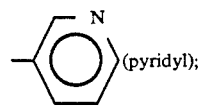

with the proviso that when $R^1$ and $R^2$ are H, halogen, alkyl, alkoxy or OH, m=1, n=3, the broken line does not represent a bond and Q is imidazolyl, $R^3$ and $R^4$ may not both be H;

and also pharmaceutically acceptable salts.

6 Claims, No Drawings

TRICYCLIC AROMATASE INHIBITORS

The invention relates to tricyclic aromatase inhibitors, their preparation and their use in a pharmaceutical preparation.

The compounds according to the invention possess the general formula I

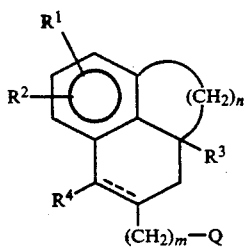

wherein
$R^1$ and $R^2$ independently of one another denote H, halogen, alkyl, alkoxy, alkythio, OH, CN, $CF_3$, $NO_2$, an amino group which is unsubstituted or substituted by alkyl, an NH acyl group, carbonamide or a free or esterified carboxylate group;
$R^3$ is H, alkyl, alkoxyalkyl or arylalkyl;
$R^4$ is H, OH, alkoxy or arylalkoxy;
m is 1 or 2;
n is 2, 3 or 4;
the broken line represents an optional bond;
Q denotes

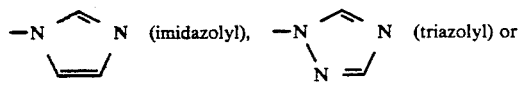

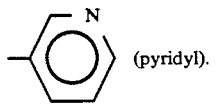

with the proviso that when $R^1$ and $R^2$ are H, halogen, alkyl, alkoxy or OH, m=1, n=3, the broken line does not represent a bond and Q is imidazolyl, $R^3$ and $R^4$ may not both be H;

also pharmaceutically acceptable salts.

The compounds according to the invention have an interesting pharmacological activity as aromatase inhibitors. In patients these compounds can prevent the conversion of androgens to estrogens, by virtue of which they can be used in combating various clinical pictures, including gynecomastia, hypertrophy of the prostate, endometriosis and estrogen-dependent types of cancer, such as breast cancer and cancer of the endometrium.

The expression alkyl in formula I denotes saturated alkyl groups having 1 to 6 carbon atoms, such as methyl, ethyl, propyl, isopropyl, butyl, tert-butyl, pentyl, hexyl and the like.

The same definition of alkyl applies in the expressions alkoxy, alkylthio, alkoxyalkyl, arylakyl and arylalkoxy.

The expression acyl denotes the group alkyl-CO, wherein alkyl has the above meaning. The carboxylate group can be esterified with alkyl alcohols, wherein the term alkyl again has the above meaning. The expression aryl in the terms arylalkyl and arylalkoxy denotes aromatic groups, preferably pyridyl, phenyl and naphthyl, which if appropriate can be substituted by OH, halogen, CN, alkyl or alkoxy.

The compounds according to the invention also include the acid addition salts of the compounds of formula I. Salts of this type are derived from mineral acids such as hydrochloric acid, sulphuric acid, phosphoric acid and the like or from organic acids such as acetic acid, citric acid, lactic acid, methanesulphonic acid, maleic acid, fumaric acid, tartaric acid, benzoic acid and the like.

When the compounds of formula I contain a free carboxylate group, the salts derived from metal hydroxides and in particular Na, K, Ca and Mg salts, and salts with quaternary ammonium compounds also fall within the scope of the invention.

Compounds of the formula I wherein $R^1$ is H or halogen, $R^2$ is H, $R^4$ is H, m is 1, n is 3, Q is imidazolyl and $R^3$ and the broken line have the meaning indicated in formula I and also their acid addition salts are considered to be amongst the compounds which are preferred.

In particular, the compounds of formula I wherein $R^1$ is halogen on position 7, $R^2$ and $R^4$ are hydrogen, m is 1, n is 3, Q is imidazolyl, $R^3$ is alkyl having 1 to 3 carbon atoms, and preferably ethyl, and the broken line represents a bond, and also their acid addition salts, are potent aromatase inhibitors. The same holds for these compounds without the optional bond, in which the substituent on positions 2 and 3a have the trans configuration and the halogen is attached at position 9.

Compounds of formula I can be prepared by methods analogous to those which are customary for the synthesis of related compounds.

A suitable starting material for making the compounds in question is the compound of general formula II.

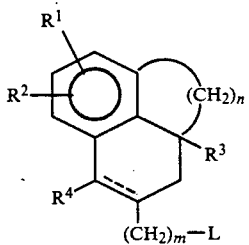

wherein $R^1$, $R^2$, $R^3$, $R^4$, m, n and the broken line have the meaning indicated in formula I and L represents a leaving group, for example a tosyl or mesyl group or a halogen.

Starting material II is made to react with imidazole, triazole or pyridine (the heterocyclic compound) in a suitable solvent, for example dimethylformamide, and warmed if necessary, after which compounds of formula I are formed. The reaction can also take place without solvent in a melt.

In order to obtain a good reaction, the heterocyclic compound can be brought into an activated form, for example in the form of a metal salt, such as the sodium salt. Salts of this type are prepared in a conventional manner, for example by reaction of a strong base, such as sodium hydride, with the heterocyclic compound.

After their synthesis, compounds of the formula I can, if necessary, be converted to an acid addition salt in the conventional manner.

It is also possible to convert compounds of formula I into another compound of the general formula I. Thus, for example, a cyano group can be converted to a carboxylate group or its ester, and a nitro group can be reduced to the amine, after which alkylation or reductive alkylation, in turn, yields an alkylated amine.

Compounds of the general formula I in which the broken line represents a bond can be prepared easily starting from compounds of formula I without the extra bond and in which $R^4$ is OH, by, for example, warming these in an acidic medium.

Compounds of this type can also be obtained by starting from compounds of the general formulae I or II (without extra bond) wherein the geminal position relative to $R^4$ or the groups $-(CH_2)_m-Q$ or $-(CH_2)_m-L$ is taken up by a hydroxyl group, and warming the starting materials in an acid medium.

Compounds of the general formula II in which m is 1 are suitable to serve as starting material for compounds of the general formula I wherein m is 2. By chain propagation in accordance with known organic chemical principles, it is possible in this way to convert compounds of formula II in which m is 1 to compounds of formula II in which m is 2. This is illustrated in more detail in Flow Sheet B and in the examples.

Starting materials of the general formula II can be synthesized in various manners known in organic chemistry. A suitable method of preparation is shown in Flow Sheet A.

Yet another route to some of the compounds is outlined in Flow Sheet C. The known phenalenone 19 is converted into the keto ester 20 and then reduced with e.g. sodiumborohydride to provide a mixture of diols and of hydroxy esters (27 and 28). These two classes of substances may readily be separated by chromatography. The hydroxy esters upon treatment with e.g. p-toluenesulphonic acid in toluene or with trifluoroacetic acid provide the $\alpha,\beta$-unsaturated ester 29. Catalytic reduction (when $R^1$ is not halogen) or magnesiummethanol reduction (preferred when $R^1$ is halogen) provides the saturated ester 30. which upon treatment with lithium aluminum hydride or another suitable reducing agent provides the cis alcohol 31. Treatment of the alcohol with e.g. tosylchloride, followed by reaction with a metal salt of imidazole provides the required imidazolyl derivative 33.

The diol mixture 27 predominantly consists of two products with the hydroxymethyl group trans to the angular substituent. Treatment of 27 with tosylhalogenide provides the monotosylate 21 which upon reaction with e.g. sodiumimidazolide in N,N-dimethylformamide affords product 22 and oxetane 23 which are readily separated by chromatography.

In cases where $R^1$ is not halogen, the remaining benzylic hydroxy group can be removed by a catalytic reduction (e.g. $H_2-Pd/C$ in acetic acid) to give 26. Alternatively, the oxetane 23 may be converted into the trans alcohol 25 by treatment with diisobutyl aluminum hydride, after which treatment with tosyl halogenide and a metal salt of imidazole gives 26.

Upon treatment of hydroxy imidazolide 22 with acid (e.g. p-toluenesulphonic acid in refluxing toluene) the unsaturated product 24 is obtained.

Another method of preparation is the construction of the heterocyclic ring Q from a suitable amine or hydrazine, in accordance with generally known principles of organic chemistry, starting from starting materials of formula II wherein L denotes $NH_2$ or $NHNH_2$.

Thus, imidazole compounds according to the invention can be made by a Marckwald reaction in which an amine is converted to an $\alpha$-aminoaldehyde, followed by condensation with potassium isothiocyanate and splitting off of the thiol group (a):

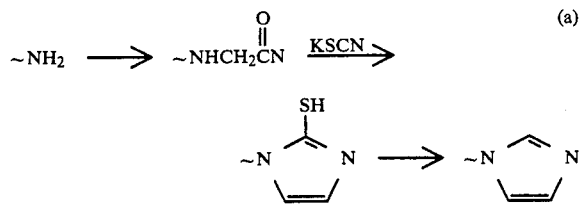

(Rodds's Chemistry of Carbon Compounds, 2nd Edition, vol IV, Part C, p 122).

Triazole compounds according to the invention can be prepared from a hydrazine and 1,3,5-triazine or 2,4,6-trichloro-1,3,5-triazine/dimethylformamide (b):

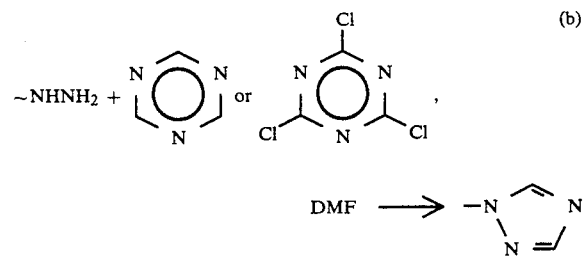

(Comprehensive Heterocyclic Chemistry, Ed. A. R. Katritzky and C. W. Reese, Vol. 5, p. 766).

The compounds of general formula I contain two or three chiral carbon atoms. The various enantiomers and diastereomers which can be formed also fall within the scope of the invention, those in the form of the pure stereo-isomers and in the form of mixtures or racemates. Pure stereo-isomers can be obtained by stereo-selective synthesis or by resolution of racemic end products or precursors thereof.

The compounds according to the invention can be processed to pharmaceutical preparations for enteral administration, local application or parenteral administration by mixing with suitable auxiliaries. A suitable form for administration is a tablet, pill, powder, capsule, paste, spray, ointment, suppository, solution, suspension or emulsion.

The compounds are usually administered in a dosage of between 0.01 and 10 mg per kg body weight. For administration to humans, the dosage is usually between 1 and 500 mg per day and preferably between 15 and 250 mg per day.

The following examples serve to illustrate the invention.

EXAMPLE 1

(See Flow Sheet A for numbers of the compounds).

a) 1-Cyano-1,2,3,4-tetrahydro-1-methylnaohthalene (2)

3.14 g 1-cyanotetraline was added at $-70°$ C. to a solution of lithium diisopropylamide (prepare from 2.12 g diisopropylamine and 13.1 ml 1.6M butyl lithium) in 30 ml dry THF (tetrahydrofuran). After 15 minutes a solution of 2.5 ml methyl iodide in 10 ml dry THF was then added. After stirring at $-70°$ C. for 1 hour, the reaction mixture was warmed to room temperature and then poured into 250 ml of water. The product was extracted with ether. The organic layer was washed with 2N HCl and water and then dried and evaporated. The residue was chromatographed and yielded 3.1 g of product 2; $R_f=0.35$ (hexane/ethyl acetate 9/1).

b) 1,2,3,4-Tetrahydro-1-methylnaphthalene-1-carboxaldehyde (3)

One equivalent of 1.2M diisobutylaluminium hydride solution in toluene was added dropwise at −70° C. to a solution of 17.4 g of 2 in 100 ml dry toluene. After stirring at −70° C. for 1 hour, 300 ml 2N hydrochloric acid was added to the reaction mixture and the resulting mixture was stirred for 15 minutes at room temperature. The organic phase was washed several times with water, dried and evaporated. This yielded 10.9 g of 3 as an oily product; $R_f=0.42$ (hexane/ethyl acetate 9/1).

c) 3-(1,2,3,4-Tetrahydro-1-methylnaphth-1-yl)-acrylic acid ethyl ester (4)

13.7 ml triethyl phosphonoacetate in 20 ml THF was added dropwise at 0° C. to a suspension of 3.20 g 60% NaH (in oil) in 60 ml THF. 9.9 g of 3 in 20 ml THF was then added dropwise in the course of 5 minutes. After stirring for 2 hours at room temperature the mixture was poured into 500 ml ice-water and the product was extracted with ether. The organic layer was washed with water, dried and evaporated. The residue was chromatographed and yielded 12.3 g of 4 as a colourless oil; $R_f=0.24$ (hexane/ethyl acetate 95/5).

d) 3-(1,2,3,4-Tetrahydro-1-methylnaphth-1-yl)-propionic acid ethyl ester (5)

A solution of 21 g of 4 in 200 ml ethanol was hydrogenated in the presence of 2 g 5% Pd on carbon. After the take-up of hydrogen was complete, the catalyst was filtered off and the filtrate evaporated. This yielded 21 g of colourless oil; $R_f=0.42$ (hexane/ethyl acetate 9/1).

e) 3-(1,2,3,4-Tetrahydro-1-methylnaphth-1-yl)-propionic acid (6)

A solution of 14 g NaOH in 60 ml of water was added to a solution of 21 g of 5 in 600 ml ethanol. The mixture was stirred for 2 hours. The bulk of the ethanol was then evaporated and the residue poured into 1 liter of water. The mixture was acidified with 2N HCl and the product extracted with ether. The organic layer was dried and evaporated. This yielded 17.5 g of carboxylic acid 6 in the form of an oil; $R_f=0.47$ (toluene/ethyl acetate/ethanol/acetic acid 8/2/1/0 1).

f) 2,3,3a,4,5-Hexahydro-1H-phenalen-1-one (7)

16 g of carboxylic acid 6 was heated at 120° C. in 200 g polyphosphoric acid for half an hour. The mixture was then cooled to about 50° C. and poured into ice-water (2 liters).

The product was extracted with ether. After washing, drying and evaporating the organic phase, the crude material obtained was purified by chromatography over silica gel and yielded 14 g of ketone 7. $R_f=0.52$ (hexane/ethyl acetate 8/2).

g) Ethyl 2,3,3a,4,5,6-hexahydro-3a-methyl-1-oxo-1H-phenalene-2-carboxylate (8)

A solution of 13.8 g of ketone 7 in 30 ml dry THF was added dropwise to a mixture of 11 g 60% NaH dispersion and 33 ml diethyl carbonate in 90 ml dry THF at 60° C. The reaction mixture was refluxed for 2 hours and 20 ml of acetic acid was then added dropwise at 0° C. The whole was then poured into 500 ml of ice-water and the product was extracted with ether. The organic phase was washed, dried and evaporated. The residue was purified by chromatography and yielded 19.2 g keto-ester 8 in the form of an oil; $R_f=0.45$ (hexane/ethyl acetate 95/5).

h) Ethyl 2,3,3a,4,5,6-hexahydro-3a-methyl-1H-phenalene-2-carboxylate (9a/9b)

A solution of 2.7 g of 8 in 27 ml acetic acid and 0.1 ml 70% perchloric acid was hydrogenated in the presence of 0.5 g 5% Pd on carbon.

After the desired amount of hydrogen (about 500 ml) had been taken up, the catalyst was filtered off and the filtrate poured into 200 ml of water. The product was extracted with ether.

The organic layer was washed with water, 10% NaHCO3 solution and water and then dried and concentrated. This yielded a crude reaction mixture consisting of 9a (trans-ester) and 9b (cis-ester). These were separated by chromatography to give 1.42 g of 9a and 0.4 g of 9b. $R_f$ (9a)=0.45 (hexane/ethyl acetate 95/5); $R_f$ (9b)=0.48 (hexane/ethyl acetate 95/5).

i) trans-2,3,3a,4,5,6-Hexahydro-3a-methyl-1H-phenalene-2-methanol (10)

A solution of 1.25 g of 9a in 10 ml THF was added dropwise to 0.4 g LiAlH4 in 10 ml THF at room temperature. After stirring for 1 hour, 0.4 ml of water, 0.4 ml of 15% NaOH and 1.2 ml of water were added successively to the reaction mixture.

After stirring for 10 minutes, the precipitate of aluminates was filtered off and the filtrate evaporated; this yielded 1.0 g of 10 in the form of a viscous oil; $R_f=0.37$ (hexane/ethyl acetate 7/3).

j) trans-2-Bromomethyl-3a-methyl-2,3,3a,4,5,6-hexahydro-1H-phenalene (11)

One equivalent of bromine was added dropwise to a solution of 1.5 g triphenylphosphine in 10 ml CH2Cl2. A solution of 0.9 g of 10 in 2 ml CH2Cl2 was then added. The mixture was stirred for 1 hour and then washed with water and 5% Na2SO3 solution. The organic phase was dried and evaporated and the residue stirred with ether/hexane (1/1).

The precipitate was filtered off (triphenylphosphine oxide) and the filtrate concentrated. The residue was purified by chromatography and yielded 1.05 g of 11; $R_f=0.26$ (hexane).

k) trans-1-(2,3,3a,4,5,6-hexahydro-3a-methyl-1H-phenalen-2-ylmethyl)-1H-imidazole hydrochloride (12)

100 mg 60% NaH (dispersion in oil) was added to a solution of 300 mg imidazole in 4 ml DMF (dimethylformamide). The mixture was stirred for ½ an hour. A solution of 1 g of the bromide of 11 in 4 ml DMF was then added.

The mixture was stirred for 3 hours and then poured into 60 ml of water. The product was extracted with ether and the extract was washed, dried and then treated with a solution of HCl gas in isopropanol until weakly acidic. The precipitate was filtered off and dried and yielded 820 mg of 12 (HCl salt). m.p. 197°–199° C. $R_f$=0.39 (ethyl acetate/methanol 9/1).

EXAMPLE 2

The following compounds were prepared in a manner analogous to that described in Example 1:

cis-1-(2,3,3a,4,5,6-hexahydro-3a-methyl-1H-phenalen-2-ylmethyl)-1H-imidazole hydrochloride. m.p. 198°–200° C.

cis-1-(2,3,3a,4,5,6-hexahydro-1H-phenalen-2-ylmethyl)-1H-1,2,4-triazole. m.p. 67° C.

trans-1-(2,3,3a,4,5,6-hexahydro-3a-methyl-1H-phenalen-2-ylmethyl)-1H-imidazole hydrochloride. m.p. 197°–199° C.

trans-2,3,3a,4,5,6-hexahydro-2-(1-imidazolylmethyl)-1H-phenalen-1-ol. m.p. 217° C. (dec.).

(1α,2β,3aα)-1-[1-(4-chlorophenylmethoxy)-2,3,3a,4,5,6-hexahydro-1H-phenalen-2-ylmethyl]-1H-imidazole hydrochloride. m.p. 91° C. (dec.).

(1α,2β,3aα)-1-[1-(4-cyanophenylmethoxy)-2,3,3a,4,5,6-hexahydro-1H-phenalen-2-ylmethyl]-1H-imidazole hydrochloride. m.p. 85° C. (dec.).

(1α,2β,3aα)-1-[1-(4-chlorophenylmethoxy)-7-chloro-2,3,3a,4,5,6-hexahydro-1H-phenalen-2-ylmethyl]-1H-imidazole hydrochloride. m.p. 162°–165° C.

(1α,2β,3aα)-1-[1-(3,4-dichlorophenylmethoxy)-2,3,3a,4,5,6-hexahydro-1H-phenalen-2-ylmethyl]-1H-imidazole hydrochloride. m.p. 155° C.

(1α,2β,3aα)-1-[1-(phenylmethoxy)-2,3,3a,4,5,6-hexahydro-1H-phenalen-2-ylmethyl]-1H-imidazole hydrochloride, m.p. 107° C.

trans-1-(9-chloro-2,3,3a,4,5,6-hexahydro-1H-phenalen-2-ylmethyl)-1H-1,2,4-triazole hydrochloride. m.p. 130° C.

trans-1-(7-chloro-2,3,3a,4,5,6-hexahydro-3a-methyl-1H-phenalen-2-ylmethyl)-1H-imidazole hydrochloride.

trans-1-(2,3,3a,4,5,6-hexahydro-3a-ethyl-1H-phenalen-2-ylmethyl)-1H-imidazole hydrochloride. m.p. 230° C.

trans-1-(2,3,3a,4,5,6-hexahydro-3a-butyl-1H-phenalen-2-ylmethyl)-1H-imidazole hydrochloride. m.p. 238° C.

trans-1-(7-cyano-2,3,3a,4,5,6-hexahydro-1H-phenalen-2-ylmethyl)-1H-imidazole hydrochloride.

trans-3-(2,3,3a,4,5,6-hexahydro-1H-phenalen-2-ylmethyl-pyridine.

trans-1-(1,2,3,3a,4,5-hexahydro-acenaphthylen-4-ylmethyl)-1H-imidazole hydrochloride. m.p. 245° C.

trans-1-(4,5,6,6a,7,8,9,10-octahydro-cyclohepta[de]-naphthalen-5-ylmethyl)-1H-imidazole hydrochloride. m.p. 243° C.

EXAMPLE 3

(See Flow Sheet B for numbers of the compounds).

a)
cis-2,3,3a,4,5,6-Hexahydro-2-1H-phenaleneacetonitrile (14)

A solution of 1.6 g cis-2-bromomethyl-2,3,3a,4,5,6-hexahydro-1H-phenalene 13 and 330 mg NaCN in 7 ml DMSO (dimethylsulphoxide) was heated at 80°–85° C. for 4 hours. The reaction mixture was then poured into 50 ml water and the product extracted with ether. The organic layer was washed with water, dried and evaporated. This yielded 1.2 g of the nitrile 14.

b) cis-2,3,3a,4,5,6-Hexahydro-2-1H-phenaleneacetic acid (15)

A solution of 1.2 g of nitrile 14 and 2 g KOH in 10 ml 70% aqueous alcohol was refluxed for 24 hours. The mixture was concentrated in a rotary evaporator to half the original volume and then diluted with 30 ml water. The aqueous layer was extracted twice with ether and then acidified with 6N HCl. The product was extracted with ether. The organic layer was washed, dried and evaporated. The residue was triturated with hexane and yielded 0.9 g of carboxylic acid 15: m.p. 115°–116° C.

c)
cis-2-(2,3,3a,4,5,6-Hexahydro-2-1H-phenalene)-ethanol (16)

A solution of 1.05 g of carboxylic acid 15 in 15 ml ether was added dropwise to a solution of 400 mg LiAlH$_4$ in 30 ml ether. The mixture was then refluxed for 2 hours and then 0.4 ml water, 0.4 ml 15% NaOH and 1.2 ml water were added successively. The precipitate formed was filtered off over Hyflo and the filtrate was evaporated. This yielded 0.95 g of alcohol 16 in the form of an oil; $R_f$=0.30 (toluene/ethanol 8/2).

d) cis-2-(2,3,3a,4,5,6-Hexahydro-2-1H-phenalene)-ethyl bromide (17)

A mixture of 0.95 g of alcohol 16 and 5 ml 48% HBr was refluxed for 6 hours. The mixture was then diluted with 30 ml water and the product was extracted with ether. The organic layer was washed with NaHCO$_3$ solution, dried and evaporated. The residue was chromatographed over silica gel (hexane as eluant) and yielded 1.1 g of bromide 17 in the form of an oil; $R_f$=0.34 (hexane).

e)
cis-1-(2,3,3a,4,5,6-Hexahydro-1H-phenalen-2-ylethyl)-1H-imidazole hydrochloride (18)

50 mg 60% NaH (suspension in oil) was added to a solution of 120 mg imidazole in 4 ml DMF. The reaction mixture was stirred for half an hour and a solution of 290 mg of bromide 17 in 3 ml DMF was then added. The mixture was stirred for 2 hours and then poured into water (30 ml).

The product was extracted with ether. The organic layer was washed with water, dried and evaporated. The residue was chromatographed over silica (hexane/ethyl acetate/ethanol 5/5/1). The product thus obtained (free base) was dissolved in 5 ml ether and a solution of HCl gas in ether was then added dropwise until the solution was weakly acid. The precipitate was filtered off and dried and yielded 260 mg of product 18; m.p. 112°–114° C.

EXAMPLE 4

The following compounds were prepared in a manner analogous to that described in Example 3:

cis-1-(2,3,3a,4,5,6-hexahydro-1H-phenalen-2-ylethyl)-1H-1,2,4-triazole hydrochloride. m.p. 164° C.

cis-3-(2,3,3a,4,5,6-hexahydro-1H-phenalen-2-ylethyl)-pyridine.

1-(7-chloro-3a-ethyl-2,3,3a,4-tetrahydro-1H-phenalen-5-ylethyl)-1H-imidazole hydrochloride. m.p. 75° C.

1-(7-chloro-2,3,3a,4-tetrahydro-3a-methyl-1H-phenalen-5-ylethyl)-1H-imidazole hydrochloride. m.p. 198° C.

trans-1-(9-chloro-2,3,3a,4,5,6-hexahydro-3a-methyl-1H-phenalen-2-ylethyl)-1H-imidazole hydrochloride. m.p. 80° C.

trans-1-(9-chloro-3a-ethyl-2,3,3a,4,5,6-hexahydro-1H-phenalen-2-ylethyl)-1H-imidazole hydrochloride. m.p. 93° C.

(3aα,4α)-1-[2-(3a-butyl-2,3,3a,4,5,6-hexahydro-1H-phenalen-5-yl)ethyl]-1H-imidazole hydrochloride. m.p. 50° C.

EXAMPLE 5 trans-1-(2,3,3a,4-Tetrahydro-3a-methyl-1H-phenalen-5-ylmethyl)-1H-imidazole hydrochloride A solution of 530 mg trans-2,3,3a,4,5,6-hexahydro-2-(1-imidazolylmethyl)-3a-methyl-1H-phenalen-1-ol hydrochloride (Example 2) in 7 ml thionyl chloride was warmed at 75° C. for 20 minutes. The mixture was evaporated to dryness and 20 ml 10% sodium carbonate solution was then added and the product was extracted with ether. The organic layer was dried and evaporated and the residue purified over silica gel (toluene/ethyl acetate/ethanol 20/10/1) and the product thus obtained was converted to its HCl salt. This yielded 390 mg of product; m.p. 235° C.

EXAMPLE 6

The following compounds were prepared in a manner analogous to that described in Example 5:

trans-1-(2,3,3a,4-tetrahydro-3a-ethyl-1H-phenalen-5-ylmethyl)-1H-imidazole hydrochloride. m.p. 164° C.

trans-1-(9-chloro-2,3,3a,4-tetrahydro-3a-methyl-1H-phenalen-5-ylmethyl)-1H-imidazole hydrochloride. m.p. 193° C. (dec.).

EXAMPLE 7

(See Flow Sheet C for numbers of the compounds: in this example $R^1$ is 9-Cl and $R^3$ is $C_2H_5$).

cis-1-(9-chloro-3a-ethyl-2,3,3a,4,5,6-hexahydro-1H-phenalen-2-ylmethyl)-1H-imidazole hydrochloride To a solution of 41 g of 20 in 2 liter of a mixture of methanol-THF (2/1) were added in several portions 10 g of sodium borohydride. After stirring for 2 hr the reaction mixture was neutralized by the addition of 35 ml of acetic acid. The reaction mixture was concentrated, stirred with water and extracted with dichloromethane. The crude product then obtained was chromatographed over silicagel to give 38 g of 28.

To a solution of 13 g of 28 in 600 ml of toluene were added 1.3 g of p-toluenesulphonic acid and this mixture was refluxed for 1 hr. The reaction mixture was washed with a 10% sodium hydrogen carbonate solution and concentrated to provide 11.5 g of essentially pure 29 ($R_f$=0.44 in hexane-ethyl acetate 9:1).

To a solution of 9.8 g of 29 in 200 ml of methanol were added in several portions 10 g of magnesium turnings. When the metal was dissolved, the reaction mixture was poured into 2 l of 1N HCl and the product was extracted with ether, to give 8 g of predominantly cis-ester 30. $R_f$=0.50 (hexane ethyl acetate 9:1).

A solution of 7.8 g of 30 in 10 ml of THF was added to a suspension of 2 g of lithium aluminum hydride in 100 ml of THF. After stirring for 1 hr the mixture was treated with subsequently 2 ml of water, 2 ml of 15% NaOH and 6 ml of water. The suspension was filtered and the filtrate was concentrated to give 7 g of 31 as an oil. This material was converted into the p-nitrobenzoyl ester. This was crystallized from ether-hexane to give 4.8 g of the cis-p-nitrobenzoate; m.p. 110°–113° C. Saponification with sodium hydroxide in aqueous methanol provides 2.8 g of pure 31 as a colourless oil; $R_f$=0.3 (hexane-ethyl acetate 8:2).

Treatment of a solution of 1.4 g of 31 in 15 ml of pyridine with 2 g of tosylchloride afforded the tosylate 32; $R_f$=0.5 (hexane-ethyl acetate 9:1).

To a solution of 2 g of imidazole in 30 ml of DMF were added 0.7 g of a 60% dispersion of sodium hydride in mineral oil. After the evolution of hydrogen had ceased, a solution of 2 g of the tosylate 32 in 5 ml of DMF was added and stirring was continued overnight. The reaction mixture was diluted with 200 ml of water and the product was extracted into ether. The organic layer was dried and concentrated and then heated with hydrochloric acid gas to give 1.5 g of cis-1-(9-chloro-3a-ethyl-2,3,4a,4,5,6-hexahydro-1H-phenalen-2-ylmethyl)-1H-imidazole hydrochloride. $R_f$=0.65 (hexane-ethyl acetate ethanol 5:5:2); m.p. 120° C.

EXAMPLE 8

In a manner analogous to that described in Example 7 was prepared:

cis-1-(9-chloro-2,3,3a,4,5,6-hexahydro-3a-methyl-1H-phenalen-2-ylmethyl)-1H-imidazole hydrochloride. m.p. 222° C.

EXAMPLE 9

(See Flow Sheet C for numbers of the compounds; in this example $R^1$ is H and $R^3$ is isopropyl).

cis-1-[2,3,3a,4,5,6-hexahydro-3a-(1-methylethyl)-1H-phenalen-2-ylmethyl]-1H-imidazole hydrochloride A solution of 2,1 g of 29 was hydrogenated in 100 ml of ethyl acetate in the presence of 200 mg of 5% Pd-C, to give 2 g of pure cis ester 30. Treatment of a solution of 30 in 30 ml of dry THF with 400 mg of lithium aluminum hydride provided 1.6 g of the alcohol 31 as a colourless oil; $R_f$=0.8 (toluene-ethyl acetate 7:3).

This alcohol was converted into the tosylate by reaction with 2 g of tosylchloride in 20 ml of pyridine, to provide 2.6 g of 32; $R_f$=0.84 (toluene-ethyl acetate 9:1). Upon reaction with imidazole sodium salt in DMF, followed by treatment with HCl, 600 mg of cis-1-[2,3,3a,4,5,6-hexahydro-3a-(1-methylethyl)-1H-phenalen-2-ylmethyl]-1H-imidazole hydrochloride were obtained; m.p. 180° C.

EXAMPLE 10

The following compounds were prepared in a manner analogous to that described in Example 9.

cis-1-(2,3,3a,4,5,6-hexahydro-3a-methyl-1H-phenalen-2-ylmethyl)-1H-imidazole hydrochloride. m.p. 200° C.

cis-1-(3a-butyl-2,3,3a,4,5,6-hexahydro-1H-phenalen-2-ylmethyl)-1H-imidazole hydrochloride. m.p. 120° C.

cis-1-(1,5,6,7,7a,8,9,10-octahydrocyclohept[i,j]-napth-9-ylmethyl)-1H-imidazole hydrochloride. m.p. 212° C.

cis-1-(1,2,2a,3,4,5-hexahydroacenaphthylen-4-ylmethyl)-1H-imidazole hydrochloride. m.p. 185° C.

EXAMPLE 11

(See Flow Sheet C for numbers of the compounds; in this example $R^1$ is H and $R^3$ is isopropyl).

trans-1-[2,3,3a,4,5,6-hexahydro-3a (1-methylethyl)-1H-phenalen-2-ylmethyl]-1H-imidazole hydrochloride Treatment of a solution of 1.4 g of 20 in a mixture of 20 ml of THF, 10 ml of water and 10 ml of ethanol with 1 g of sodium borohydride in several portions followed by stirring overnight provided 1.1 g of the diol 27 as a mixture of epimeric alcohols. This was dissolved in 20 ml of pyridine and treated with 1.5 g of tosylchloride. After stirring overnight the mixture was poured into 150 ml of water and the monotosylate 21 was extracted with ethyl acetate and purified by chromatography to provide 0.8 g of essentially pure material; $R_f=0.70$ (hexane ethyl acetate 1:1).

Treatment of this with sodium imidazolide (derived from 1.1 g of imidazole and 0.3 g of 60% sodium hydride dispersion) in 10 ml of DMF, followed by work-up and treatment with hydrochloric acid in ether afforded 400 mg of 22 as HCl salt; m.p. 172° C.

Hydrogenation of this material in 10 ml of acetic acid in the presence of 100 mg of 10% Pd-C during 2 days provided 320 mg of trans-1-[2,3,3a,4,5,6-hexahydro-3a-(1-methylethyl)-1H-phenalen-2-ylmehtyl]-1H-imidazole hydrochloride as white crystalline material m.p. 220° C.

EXAMPLE 12

The following compounds were prepared in a manner analogous to that described in Example 11:

trans-1-(2,3,3a,4,5,6-hexahydro-3a-methyl-1H-phenalen-2-ylmethyl)-1H-imidazole hydrochloride. m.p. 199° C.

trans-1-(3a-ethyl-2,3,3a,4,5,6-hexahydro-1H-phenalen-2-ylmethyl)-1H-imidazole hydrochloride. m.p. 230° C.

trans-1-(3a-butyl-2,3,3a,4,5,6-hexahydro-1H-phenalen-2-ylmethyl)-1H-imidazole hydrochloride. m.p. 238° C.

EXAMPLE 13

Flow Sheet C for numbers of the compounds; in this example $R^1$ is 7-Br and $R^3$ is $C_2H_5$)

1α/β,2α,3aβ-9-bromo-3a-ethyl-2,3,3a,4,5,6-hexahydro-2-(1-imidazolymethyl)-1H-phenalen-1-ol and
1-(7-bromo-3a-ethyl-2,3,3a,4,5,6-tetrahydro-1H-phenalen-5-ylmethyl)-1H-imidazole hydrochloride A solution of 8 g of 20 in a mixture of 250 ml of methanol and 1:25 ml of THF was treated in portions with 8 g of sodium borohydride over a period of 5 hrs. After stirring overnight the mixture was treated with acetic acid to destroy residual sodium borohydride, diluted with water and extracted with ethyl acetate. Purification of the crude product by chromatography ultimately provided 6.8 g of a mixture of epimeric diols 27.

Treatment with tosylchloride in pyridine provided 7.2 g of the monotosylate 21; $R_f=0.68$ (hexane-ethyl acetate 6:4). This was reacted with sodium imidazolide (prepared from 6 g of imidazole and 2 g of 60% NaH dispersion) in 50 ml of DMF. After stirring for 16 hr the mixture was poured into water. The aqueous phase was extracted with ethyl acetate and the organic layer was washed, dried and concentrated. The residue was chromatographed to provide 2.6 g of 1α/β,2α,3aβ-3a-ethyl 2,3,3a,4,5,6-hexahydro-2-(1-imidazolylmethyl-1H-phenalen-1-ol 22 (m.p. 145° C.) and 1.2 g of the oxetane 23.

A quantity of 1 g of the hydroxy imidazolide 22 in 100 ml of toluene was treated with 1 g of p-toluenesulphonic acid and refluxed for 1 hr. The organic phase was washed with 5% sodium hydrogen carbonate solution, and then dried and concentrated. The residue was dissolved in ether and treated with hydrochloric acid gas, to give 1.6 g of 1-(7-bromo-3a-ethyl-2,3,3a,4-tetrahydro-1H-phenalen-5-ylmethyl)-1H-imidazole hydrochloride. m.p. 209° C.

EXAMPLE 14

The following compounds were prepared in a manner analogous to that described in Example 13:

1-(3a-butyl-2,3,3a,4-tetrahydro-1H-phenalen-5-ylmethyl)-1H-imidazole hydrochloride. m.p. 104° C.

1-(2,3,3a,4-tetrahydro-3a-methyl-1H-phenalen-5-ylmethyl)-1H-imidazole hydrochloride. m.p. 235° C.

1-(9-chloro-2,3,3a,4-tetrahydro-3a-methyl-1H-phenalen-5-ylmethyl)-1H-imidazole hydrochloride. m.p. 193° C.

1-(3a-ethyl-2,3,3a,4-tetrahydro-1H-phenalen-5-ylmethyl)-1H-imidazole hydrochloride. m.p. 164° C.

1-(2,3,3a,4-tetrahydro-3a-propyl-1H-phenalen-5-ylmethyl)-1H-imidazole hydrochloride. m.p. 184° C.

1-(7-chloro-3a-ethyl-2,3,3a,4-tetrahydro-1H-phenalen-5-yl methyl)-1H-imidazole hydrochloride. m.p. 216° C.

1-(7-bromo-3a-ethyl-2,3,3a,4-tetrahydro-1H-phenalen-5-yl methyl)-1H-imidazole hydrochloride. m.p. 209° C.

1-(1,2,2a,3-tetrahydroacenaphthylen-4-ylmethyl)-1H-imidazole hydrochloride. m.p. 246° C.

1-(4,5,6,7,7a,8-hexahydro-cyclohepta[i,j]naphth-9-yl methyl)-1H-imidazole hydrochloride. m.p. 213° C.

1-(7-chloro-2,3,3a,4-tetrahydro-3a-methyl-1H-phenalen-5-ylmethyl)-1H-imidazole hydrochloride. m.p. 248° C.

1-(2,3,3a,4-tetrahydro-3a-(1-methylethyl)-1H-phenalen-5-ylmethyl)-1H-imidazole Z-2-butenedioate (1:1). m.p. 110° C.

1α/β,2a,3aβ-2,3,3a,4,5,6-hexahydro-2-(1-imidazolylmethyl)-3a-(1-methylethyl)-1H-phenalen-1-ol hydrochloride. m.p. 178° C.

1α/β,2a,3aβ-3a-butyl-2,3,3a,4,5,6-hexahydro-2-(1-imidazolylmethyl)-1H-phenalen-1-ol hydrochloride. m.p. 165° C.

1α/β,2a,3aβ-9-chloro-2,3,3a,4,5,6-hexahydro-2-(1-imidazolylmethyl)3a-methyl-1H-phenalen-1-ol. m.p. 177° C.

EXAMPLE 15

(See Flow Sheet C for numbers of the compounds; in this example $R^1$ is 9-Br and $R^3$ is $C_2H_5$).

trans-1-(9-bromo-3a-ethyl-2,3,3a,4,5,6-hexahydro-1H-phenalen-2-ylmethyl)-1H-imidazole hydrochloride The oxetane 23 (200 mg; Example 13 was dissolved in 10 ml of diethylether and at −40 ° C. 2 ml of diisobutylaluminum hydride (1.2M solution in toluene) were added. After stirring for an additional hr, excess of hydride was destroyed by addition of 4N hydrochloric acid. The product was extracted with diethylether. The organic layer was washed, dried and concentrated and the residue was chromatographed to give 120 mg of the required trans alcohol 25.

This alcohol was tosylated and reacted with sodium imidazolide in DMF to provide 85 mg of trans-1-(9- bromo-3a-ethyl-2,3,3a,4,5,6-hexahydro-1H-phenalen-2-ylmethyl)-1H-imidazole hydrochloride. m.p. 231° C.

EXAMPLE 16

The following compounds were prepared in a manner analogous to that described in Example 15:

trans-1-(7-chloro-2,3,3a,4,5,6-hexahydro-3a-methyl-1H-phenalen-2-ylmethyl)-1H-imidazole hydrochloride. m.p. 236° C.

trans-1-(2,3,3a,4,5,6-hexahydro-3a-propyl-1H-phenalen-2-ylmethyl)-1H-imidazole hydrochloride. m.p. 250° C.

trans-1(4,5,6,7,7a,8,9,10-octahydro-cyclohept[i,j]naphth-9-ylmethyl)-1H-imidazole hydrochloride. m.p. 243° C.

trans-1-(1,2,2a,3,4,5-hexahydroacenaphthylen-4-ylmethyl)-1H-imidazole hydrochloride. m.p. 245° C.

trans-1-(9-chloro-3a-ethyl-2,3,3a,4,5,6-hexahydro-1H-phenalen-2-ylmethyl)-1H-imidazole hydrochloride. m.p. 223° C.

trans-1-(9-chloro-2,3,3a,4,5,6-hexahydro-3a-methyl-1H-phenalen-2-ylmethyl)-1H-imidazole hydrochloride. m.p. 236° C.

-continued
Flow Sheet A
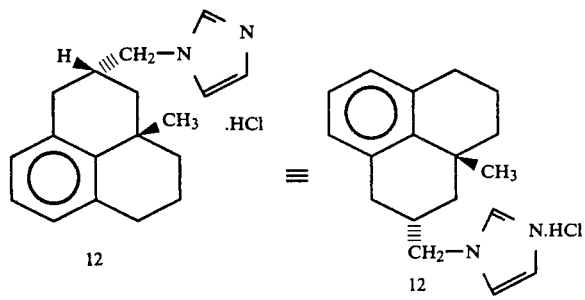
Flow Sheet B
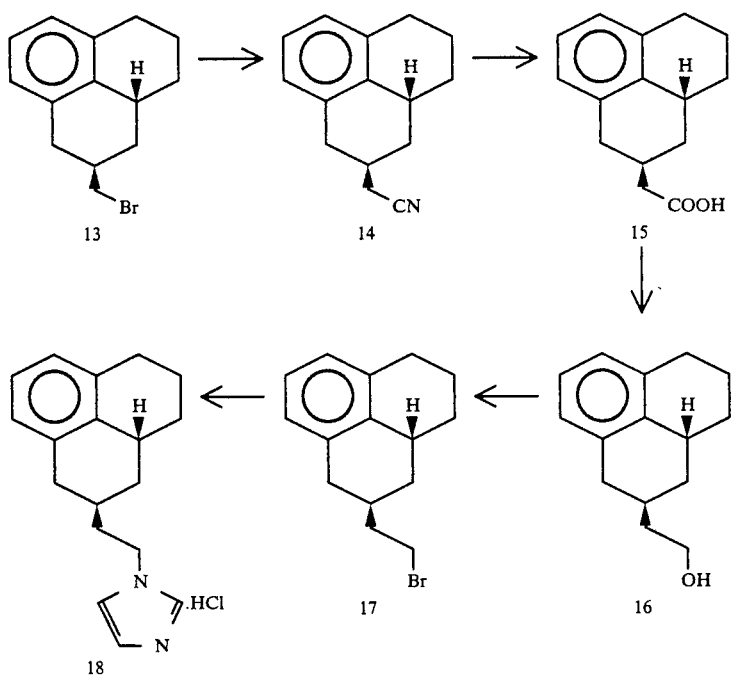
Flow Sheet C
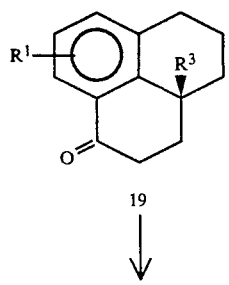

-continued
Flow Sheet C

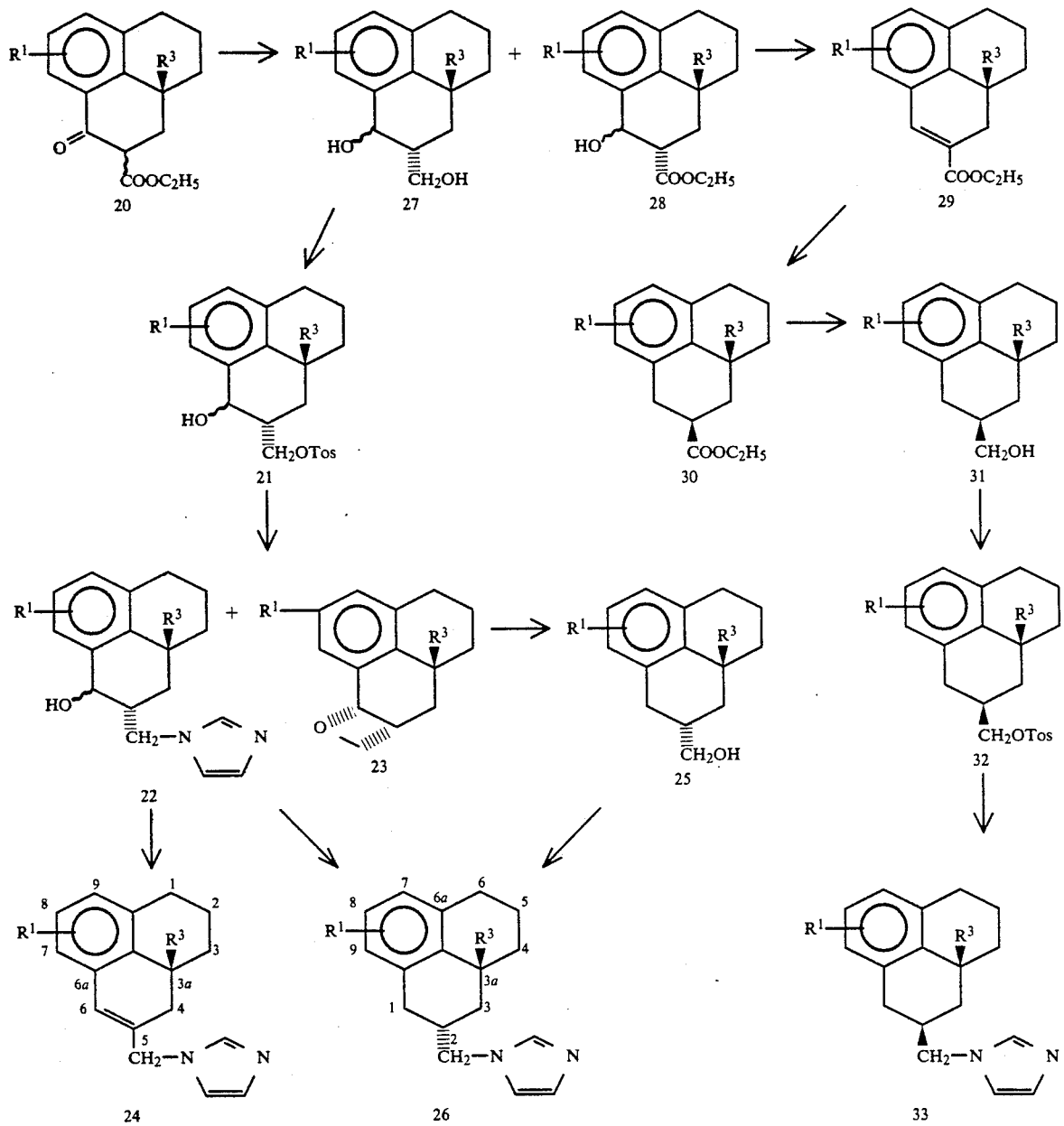

I claim:
1. A tricyclic aromatase inhibitor of the formula I

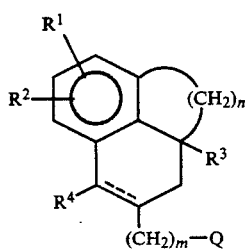

wherein
R$^1$ and R$^2$ independently of one another denote H, halogen, alkyl, alkoxy, alkylthio, OH, CN, CF$_3$, NO$_2$, and amino group which is unsubstituted or substituted by alkyl, an NH acyl group, carbonamide or a free or esterified carboxylate group;
R$^3$ is H, alkyl, alkoxyalkyl or arylalkyl;
R$^4$ is H, OH, alkoxy or arylalkoxy;
m is 1 or 2;
n is 2, 3 or 4;
the broken line represents an optional bond;
Q denotes

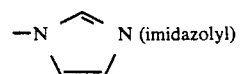 N (imidazolyl)

with the proviso that when R$^1$ and R$^2$ are H, halogen, alkyl, alkoxy or OH, m=1, n=3, the broken line does not represent a bond and Q is imidazolyl, $R^3$ and $R^4$ may not both be H, and when $R_3$ or $R_4$ is an arylalkyl it is selected from the group consisting of phenyl and naphthyl, either of which may be unsubstituted or substituted by OH, halogen, CN, alkyl or alkoxy groups; or a pharmaceutically acceptable salt thereof.

2. A compound according to claim 1, wherein $R^1$ is H or halogen, $R^2$ is H, $R^4$ is H, m is 1, n is 3, and Q is imidazolyl, or an acid addition salt thereof.

3. A compound according to claim 1, wherein $R^1$, $R^2$, and $R^4$ are H, $R^3$ is alkyl having 1 to 3 carbon atoms, m is 1, n is 3, and Q is imidazolyl, or an acid addition salt thereof.

4. A compound according to claim 2, wherein $R^1$ is halogen on position 7, $R^3$ is alkyl having 1 to 3 carbon atoms, the broken line represents a bond, or an acid addition salt thereof.

5. A compound according to claim 2, wherein $R^1$ is halogen on position 9, $R^3$ is alkyl having 1 to 3 carbon atoms, the broken line does not represent a bond and the substituents on positions 2 and 3a have the trans configuration, or an acid addition salt thereof.

6. Pharmaceutical preparation for use as an aromatase inhibitor comprising at least one compound according to claim 1 in an effective amount to provide aromatase inhibiting activity and a pharmaceutically acceptable carrier.

* * * * *